(12) United States Patent
Czerney et al.

(10) Patent No.: US 8,039,648 B2
(45) Date of Patent: Oct. 18, 2011

(54) COMPOUNDS USED AS DYES COMPERABLE TO ALEXA FLUOR 350 DYES

(75) Inventors: Peter T. Czerney, Weimar (DE); Surbhi Desai, Rockford, IL (US); Matthias S. Wenzel, Jena (DE); Boguslawa Dworecki, Rockford, IL (US); Frank G. Lehmann, Jena (DE); Bernd G. Schweder, Jena (DE); Wilhelm G. Frank, Jena (DE)

(73) Assignee: Pierce Biotechnology, Inc., Rockford, IL (US)

( * ) Notice: Subject to any disclaimer, the term of this patent is extended or adjusted under 35 U.S.C. 154(b) by 6 days.

(21) Appl. No.: 12/485,439

(22) Filed: Jun. 16, 2009

(65) Prior Publication Data

US 2010/0317045 A1      Dec. 16, 2010

(51) Int. Cl.
  *C07D 311/08*   (2006.01)
(52) U.S. Cl. ......................................................... 549/395
(58) Field of Classification Search ................... 549/395
  See application file for complete search history.

(56) References Cited

U.S. PATENT DOCUMENTS 5,696,157 A    12/1997   Wang et al.

*Primary Examiner* — Shawquia Young
(74) *Attorney, Agent, or Firm* — Thompson Hine LLP

(57) ABSTRACT

Compounds used as dyes comparable to Alexa Fluor 350 dyes. The inventive compounds have high fluorescence quantum yield and high photostability. The dyes facilitate analysis of biological structures with enhanced sensitivity and selectivity.

9 Claims, 11 Drawing Sheets
(2 of 11 Drawing Sheet(s) Filed in Color)

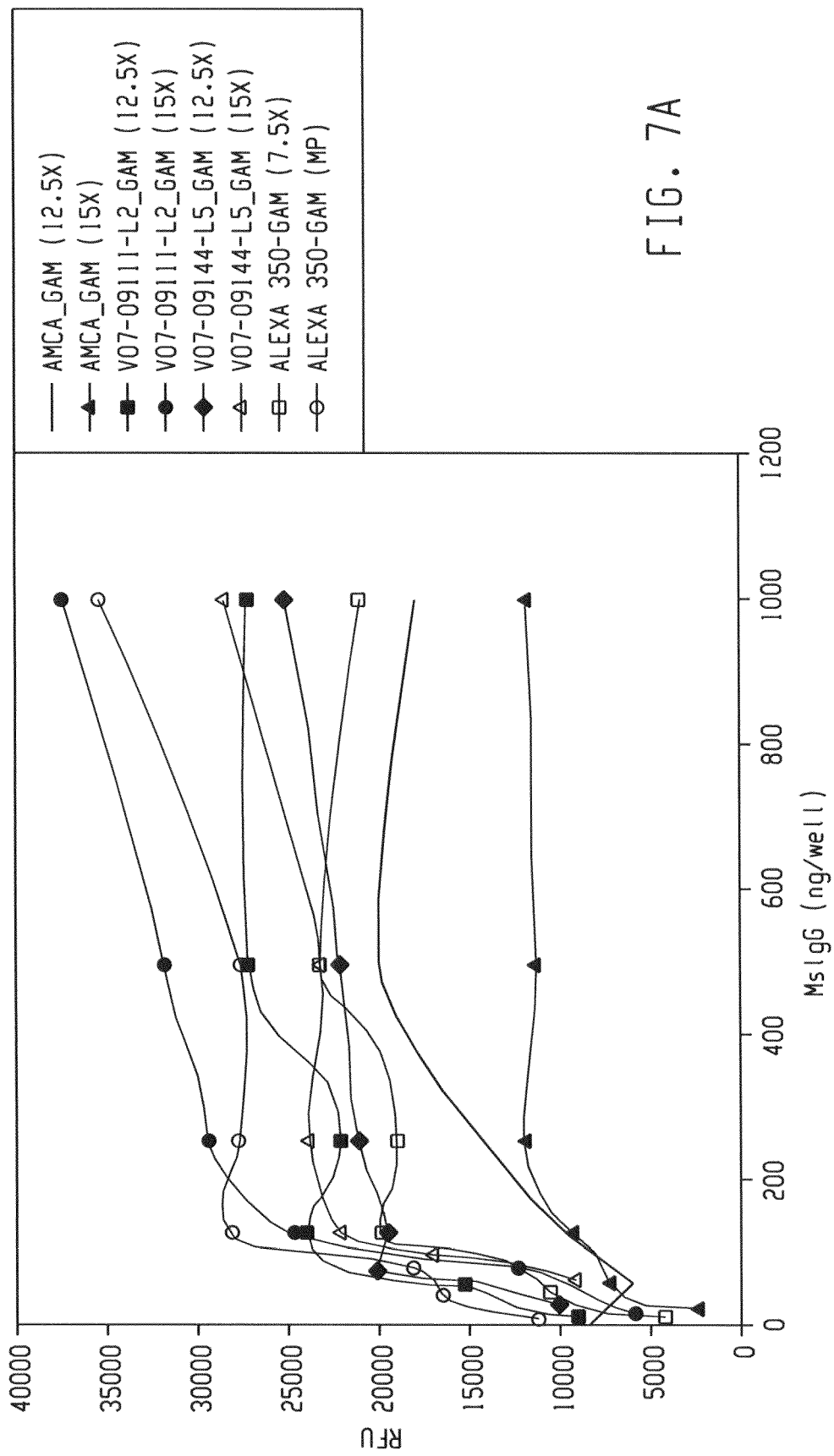

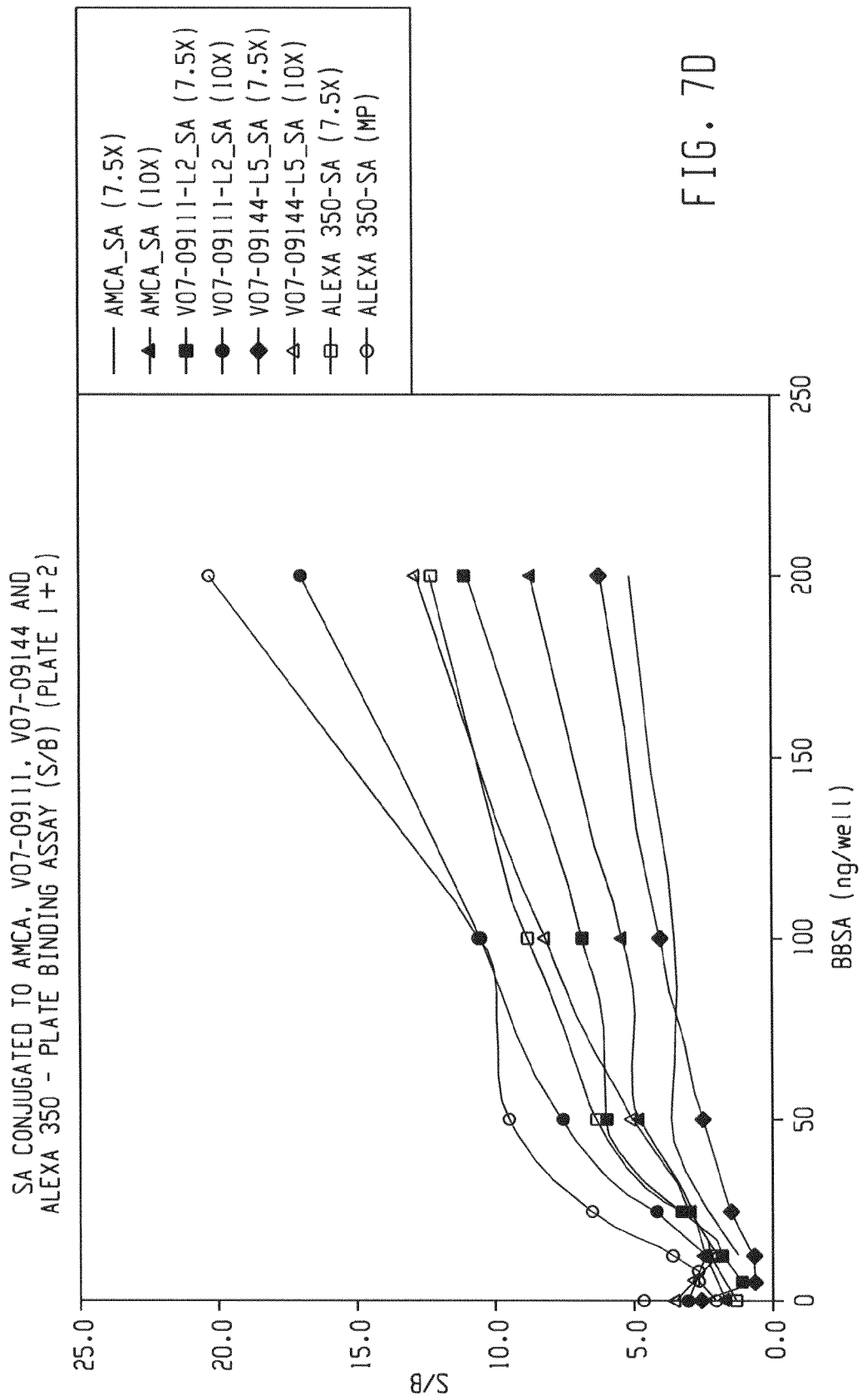

STAINING OF LAMIN A IN HELA CELLS WITH V07-09111-GAM CONJUGATES AND V07-09144-GAM CONJUGATES COMPARED TO AMCA-GAM AND ALEXA FLUOR 350-GAM

ULTRAVIOLET EXCITATION OF NHS-AMCA, V07-09111-NHS "8-ISOMER", V07-09144-NHS "6-ISOMER" AND ALEXA FLUOR 350-NHS ESTER

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: DyLight680-S- attached to guanine at location 1

<400> SEQUENCE: 1
gcctttcagg gagtatcga                                                  19

<210> SEQ ID NO 2
<211> LENGTH: 19
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (8)..(8)
<223> OTHER INFORMATION: V07-09111 is attached to thymine at location 8

<400> SEQUENCE: 2
cggaaagtcc ctcatagct                                                  19
```

COMPOUNDS USED AS DYES COMPERABLE TO ALEXA FLUOR 350 DYES

Alexa Fluor 350 has the following structure

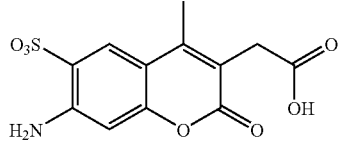

Alexa Fluor 350 dyes (Molecular Probes) belong to a series of fluorescent dyes and conjugates, useful for bioanalytical and diagnostic applications with enhanced fluorescence and photostability over other dyes. Alexa Fluor 350 dyes can be used over the pH range from about pH 4 to about pH 10. Additional dyes are desirable.

The patent or application file contains at least one drawing executed in color. Copies of this patent or patent application publication with color drawing(s) will be provided by the Office upon request and payment of the necessary fee.

Figure 6A:
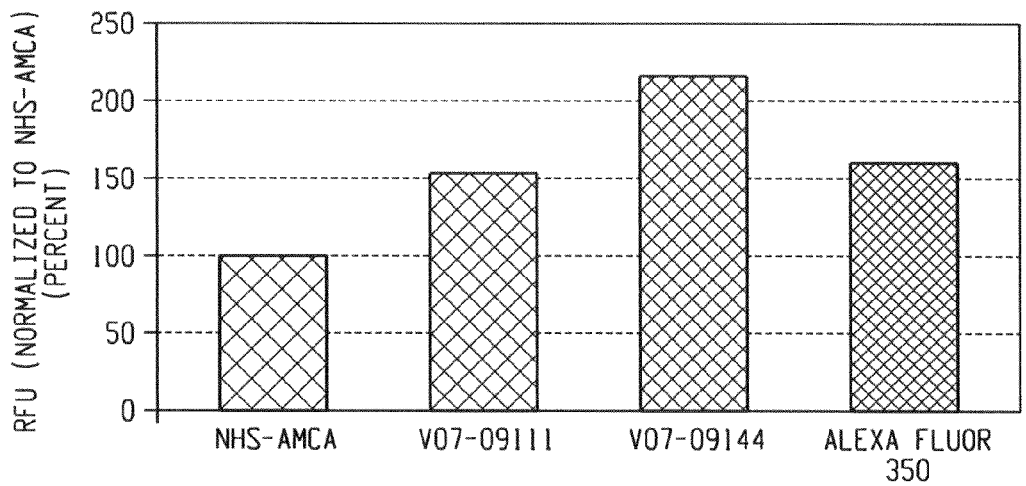
Figure 6B:
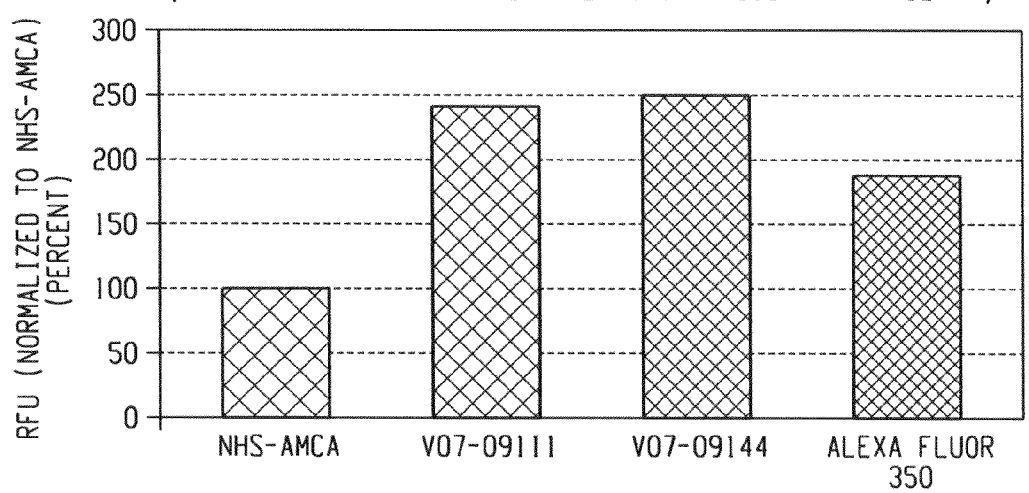

FIGS. 6A-B show fluorescence intensities of succinimidyl-7-amino-4-methylcoumarin-3-acetate (NHS-AMCA), V07-09111-NHS "8-isomer"; V07-09144-NHS "6-isomer", and Alexa Fluor 350.

FIGS. 7A-D show uses of the compounds in plate based assays.

FIGS. 8A-H show staining of Lamin A in HeLa cells with V07-09111-GAM conjugates and V07-09144-GAM conjugates compared to AMCA-GAM and Alexa Fluor 350-GAM.

FIGS. 9A-H show ultraviolet excitation of NHS-AMCA, V07-09111-NHS "8 isomer", V07-09144-NHS "6-isomer", and Alexa Fluor 350-NHS ester.

Figure 10:
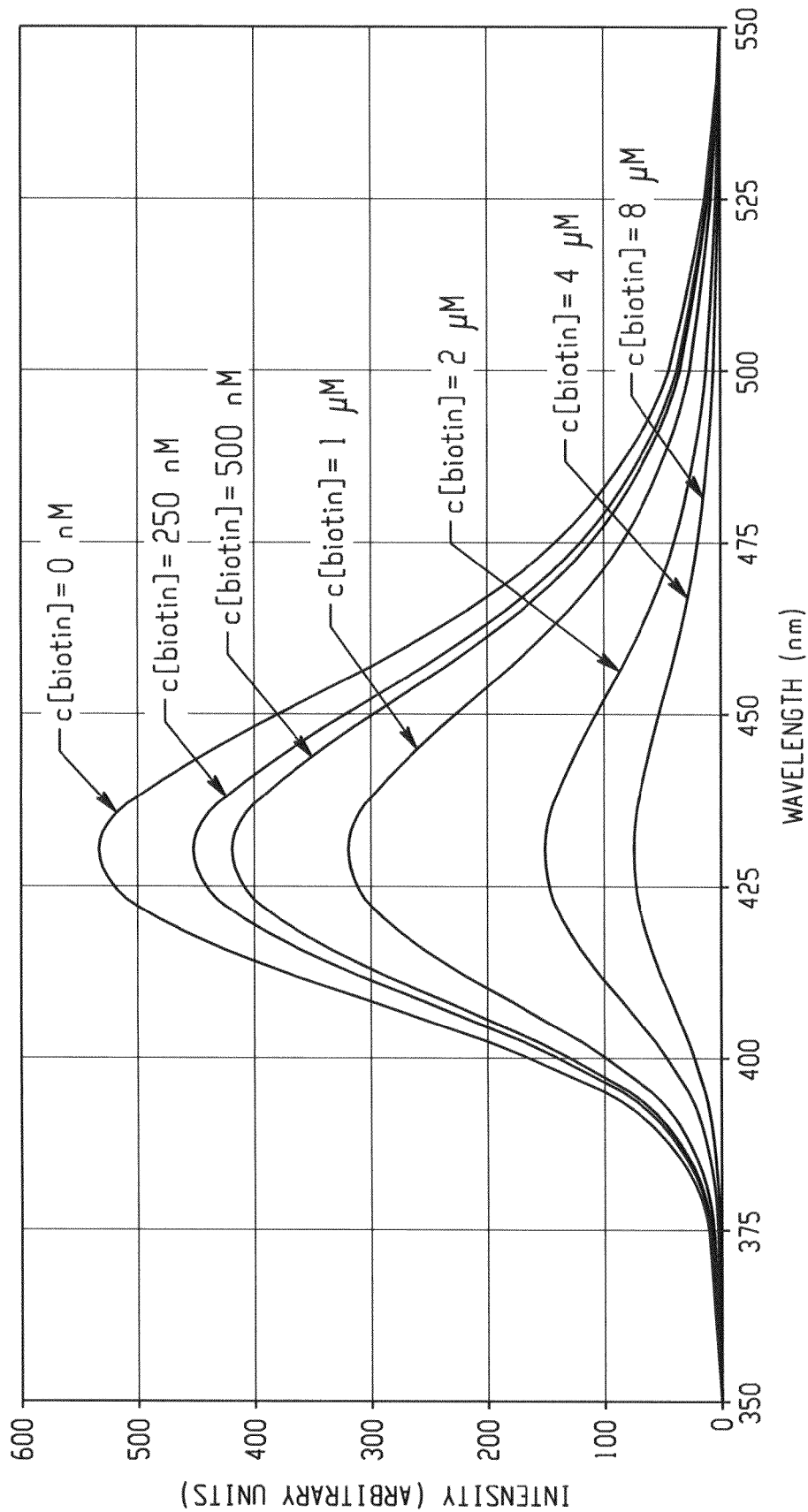

FIG. 10 shows titration of V070911-streptavidin with DY-481XL-biotin.

Compounds used as dyes comparable to Alexa Fluor 350, and compositions that contain at least one compound and at least one biocompatible excipient, are disclosed. The inventive compounds belong to the general class of sulfonated derivatives of 7-aminocoumarin, in which the coumarin moiety has a fused ring in the 3,4-position. These dyes are comparable to Alexa Fluor 350 dyes, having high fluorescence quantum yield and, for histological applications, high photostability bioanalysis, with bioanalysis including qualitative and/or quantitative processes, detection, diagnosis, etc. For example, in one embodiment, the dyes are used in tissue detection, ranging from hand-held ultraviolet light detection to high-end instrumentation light detection, and in other immunofluorescent applications. The dyes permit bioanalysis with enhanced sensitivity and selectivity.

In one embodiment, a compound has the general formula

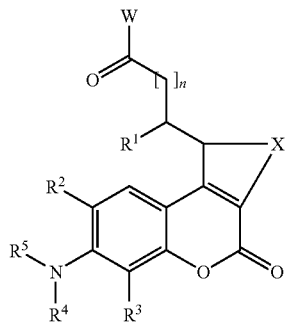

wherein each of $R^1$, $R^2$, and $R^3$ is independently selected from the group consisting of H, $C_1$-$C_{18}$ alkyl, halogen, perfluoroalkyl, CN, $NO_2$ and $SO_3M$;

M is selected from the group consisting of $H^+$ and a biologically compatible cation;

$R^2$ in combination with $R^5$ and/or $R^3$ in combination with $R^4$ are covalently connected by saturated or unsaturated aliphatic or heteroaliphatic systems' each of $R^4$ and $R^5$ is independently selected from the group consisting of H, $C_1$-$C_{18}$ alkyl, $C_1$-$C_{18}$-carboxyalkyl, $C_1$-$C_{18}$-sulfoalkyl, $C_1$-$C_{18}$ sulfatoalkyl, and $C_6$-$C_{18}$ aryl;

$R^4$ in combination with $R^5$ forms a saturated 5-7-member aliphatic or heteroaliphatic ring system that is selected from the group consisting of a piperidine, morpholine, pyrrolidine, and a piperazine; or $R^4$ in combination with $R^3$ and/or $R^5$ in combination with $R^2$ are covalently connected by saturated or unsaturated aliphatic or hereoaliphatic systems;

X is a divalent saturated or unsaturated aliphatic or heteroaliphatic group that can be substituted by at least one atom selected from the group consisting of oxygen, substituted nitrogen, and sulfur;

n is a integer from 0 to 18 inclusive, i.e., n can be 0, 1, 2, 3, 4, 5, 6, 7, 8, 9, 10, 11, 12, 13, 14, 15, 16, 17 or 18;

W is selected from the group consisting of OH, SH, $NH_2$, NH—$NH_2$, F, Cl, Br, I, hydroxysuccinimidyl/sulfosuccinimidyl (NHS), 4-sulfo-2,3,5,6-tetrafluorophenoxy (OSTP), 2,3,5,6-ttetrafluorophenoxy (OTFP), O-benzotriazole, benzotriazole, NR-L-OH, NR-L-O-phosphoamidite, NR-L-SH, NR-L-$NH_2$, NR-L-NH—$NH_2$, NR-L-$CO_2$H, NR-L-$CO_2$—NHS, NR-L-$CO_2$—STP, NR-L-$CO_2$-TFP, NR-L-CO-benzotriazole, NR-L-CHO, NR-L-maleimid, and NR-L-NH—CO—$CH_2$—I;

R is selected from the group consisting of H and $C_1$-$C_{18}$ alkyl; and

L is selected from the group consisting of a divalent linear (—$(CH_2)_o$, o=1 to 15 inclusive, i.e., o can be 1, 2, 3, 4, 5, 6, 7, 8, 9, 10, 11, 12, 13, 14, or 15), crossed, and cyclic alkylene group that can be substituted by at least one atom selected from the group consisting of oxygen, substituted nitrogen and sulfur.

As known to a person of ordinary skill in the art, a biologically compatible cation may be, e.g., Na+, K+, diethyl isopropyl ammonium (DIPEA)-$H^+$.

In one embodiment of the general formula, the compound has the formula

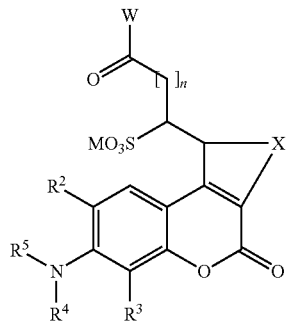

with substitutents as previously described and R¹=—SO₃M.

In one embodiment of the general formula, the compound has the formula

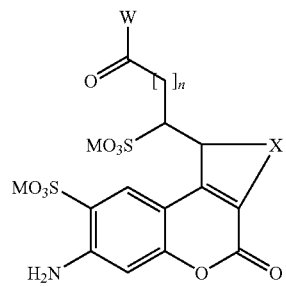

(6-isomer) with substitutents as previously described, each of R¹, R²=—SO₃M; and each of R³, R⁴, and R⁵=H. A 6-isomer defines the position of the sulfonate group (SO₃M) on the 6 carbon of the phenyl ring Examples include V07-09144 and V07-09144-NHS.

In one embodiment of the general formula, the compound has the formula

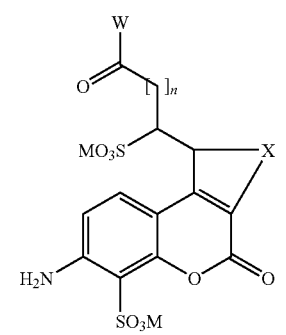

(8-isomer) with substitutents as previously described, each of R¹, R³=—SO₃M; and each of R², R⁴, and R⁵=H. A 8-isomer defines the position of the sulfonate group (SO₃M) on the 8 carbon of the phenyl ring. An example is V07-0911 and V07-09111-NHS.

In one embodiment of the general formula, the compound has the formula

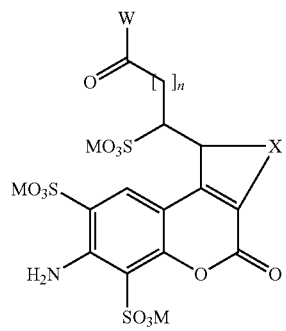

(6, 8-isomers) with substitutents as previously described, each of R¹, R², and R³=—SO₃M; and each of R⁴ and R⁵=H. A 6 and 8-isomer defines the position of the sulfonate group (SO₃M) on both the 6 and 8 carbons of the phenyl ring. An example is V07-09140.

In one embodiment of the general formula, the compound has the formula

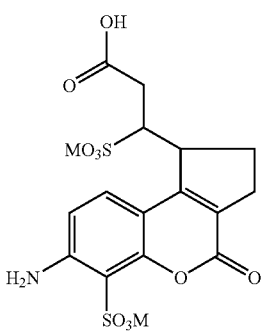

(8-isomer) with substitutents as previously described, each of R¹, R³=—SO₃M; each of R², R⁴, and R⁵=H; W=—OH; and X=—CH₂—CH₂—. An example is V07-09089, which is a DY-350 dye with no spacer. Among the DY-350 dyes, V07-09089 has a lower fluorescence intensity, has lower labeling, and has lower binding in a functional plate assay.

In one embodiment, the compound has the formula

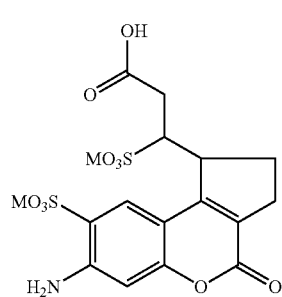

(6-isomer) with substitutents as previously described, each of R¹, R²=—SO₃M; each of R³, R⁴, and R⁵=H; W=—OH; and X=—CH₂—CH₂—. An example is V07-09142.

In one embodiment, the compound has the formula

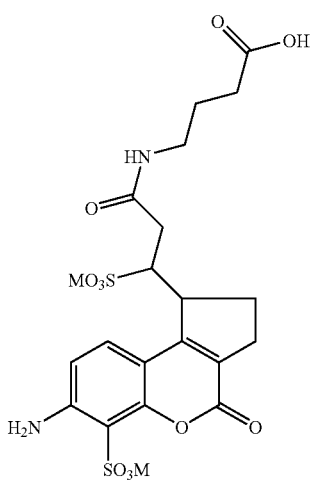

An example is V07-09111.

In one embodiment, the compound has the formula

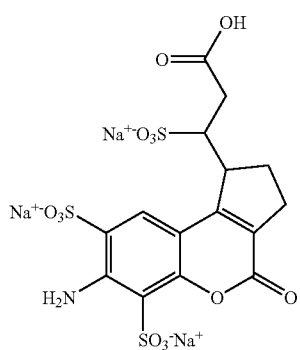

An example is V07-09140.

In one embodiment, the compound has the formula

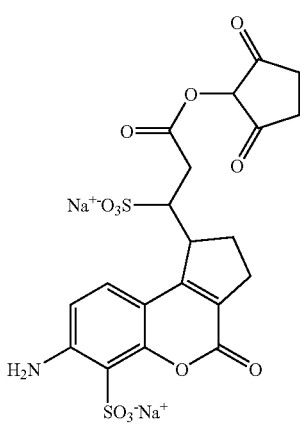

An example is V07-09089-NHS.

In one embodiment, the compound is a phosphine having the formula

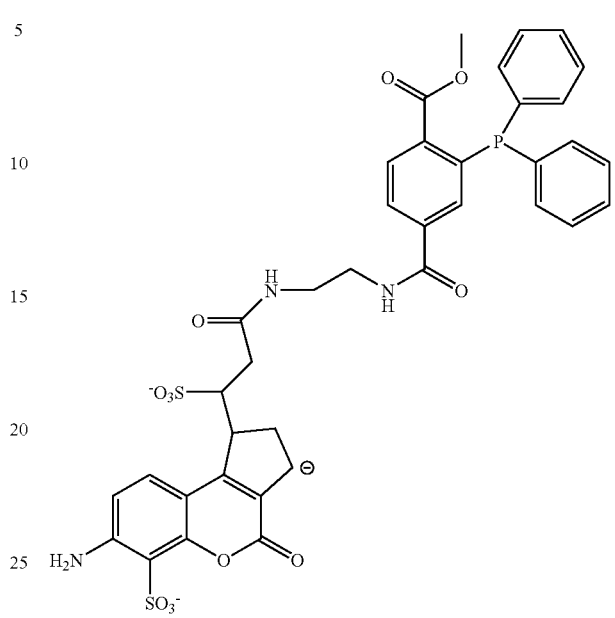

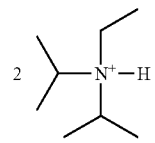

Table 1 contrasts the general formula of the inventive compounds with Alexa Fluor 350 dye compounds disclosed in U.S. Pat. No. 5,696,157. Table 2 contrasts specific inventive compounds with specific examples of Alexa Fluor 350 dyes. In the inventive compounds, X is a divalent saturated or unsaturated aliphatic or heteroaliphatic group. In the Alexa Fluor 350 compounds, $R^3$ and $R^4$ are independent and never connected. The presence of one carboxyalkyl group and two sulfo groups:

in the disclosed compounds provides it with increased solubility in water.

TABLE 1

| Inventive Compounds | Alexa Fluor 350 |
|---|---|

TABLE 1-continued

| Inventive Compounds | Alexa Fluor 350 |
|---|---|

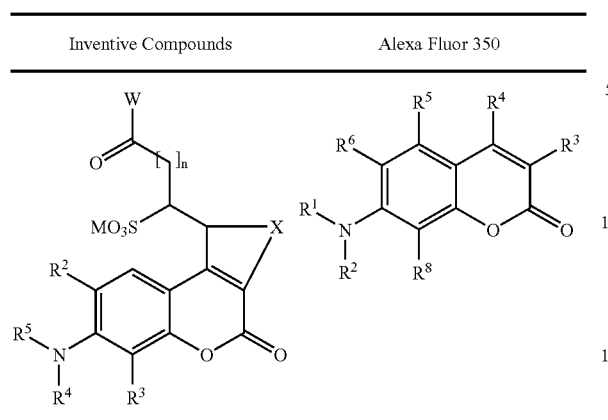

TABLE 2

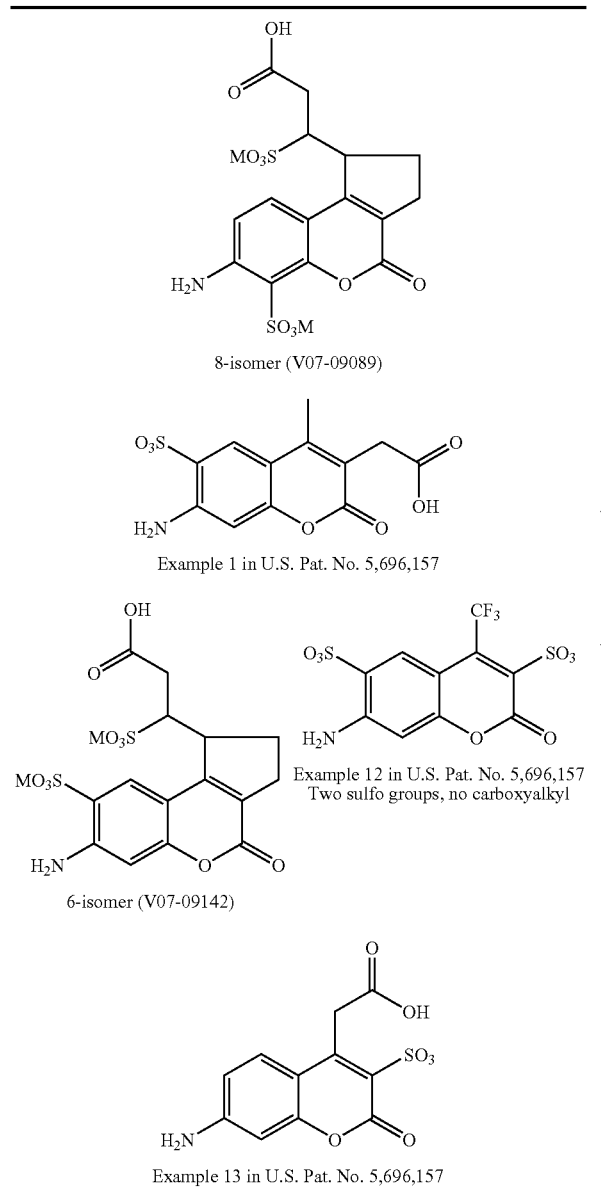

8-isomer (V07-09089)

Example 1 in U.S. Pat. No. 5,696,157

6-isomer (V07-09142)

Example 12 in U.S. Pat. No. 5,696,157
Two sulfo groups, no carboxyalkyl

Example 13 in U.S. Pat. No. 5,696,157

TABLE 2-continued

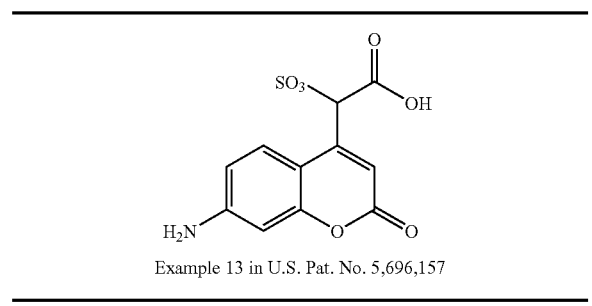

Example 13 in U.S. Pat. No. 5,696,157

Conjugates that may be used include, but are not limited to, N-hydroxysuccinimide (NHS) esters, tetrafluorophenyl esters (TFP), pentafluorophenyl esters (PFP), maleimides, pyridyldithio propionamides, iodoacetyl, hydrazides, aminoxy, amine and carboxy (for coupling with carbodiimides) derivatives.

Two inventive conjugates, a 6-isomer N-hydroxysuccinimide-ester (NHS-ester) and an 8-isomer NHS-ester:

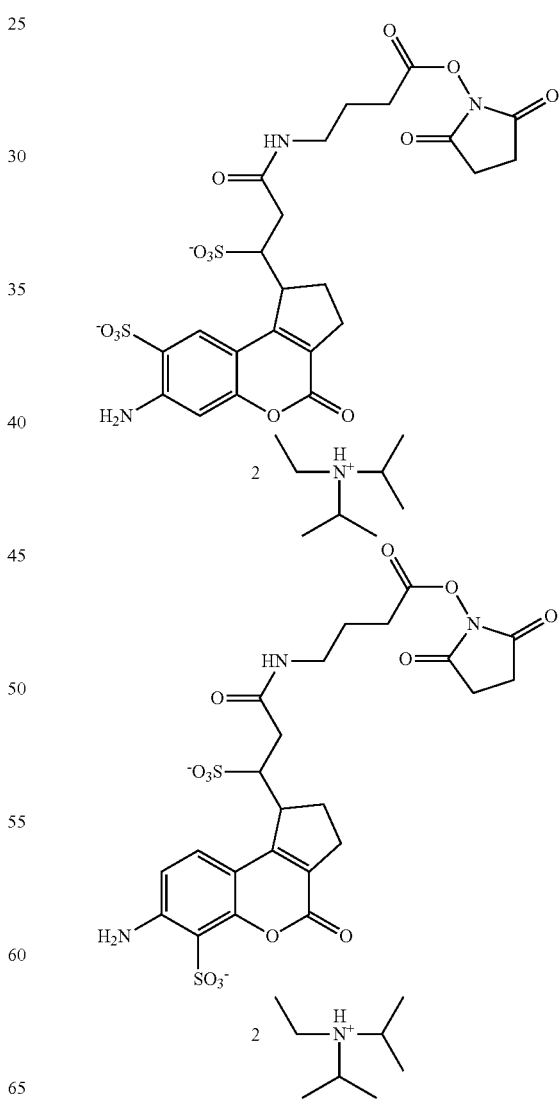

Two sample derivatives, derivatives 1 and 2 of the inventive compounds, and the NHS-ester of derivative 2, and their respective properties are shown (PBS=phosphate buffered saline).

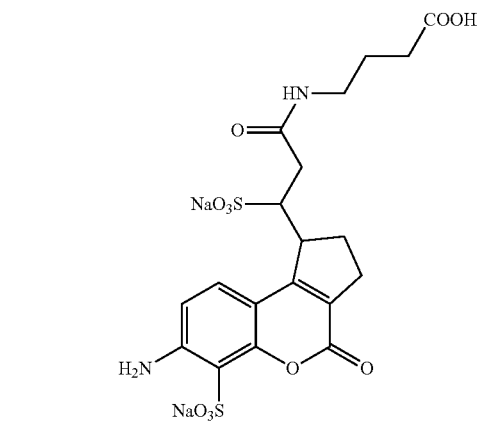

Derivative 1
VO7-09111 ($\lambda_{max}$ 354 nm; $\lambda_{em}$ 431 nm (PBS))

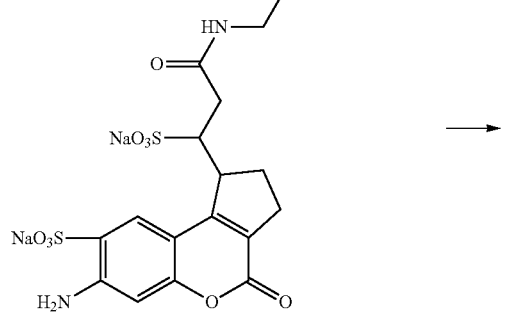

Derivative 2
V07-09144
$\lambda_{max}$ 348 nm
$\lambda_{em}$ 440 nm (PBS)

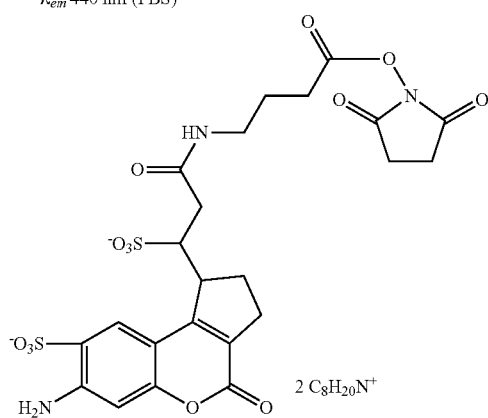

NHS-ester of
Derivative 2
V07-09144-NHS
$\lambda_{max}$ 349 nm
$\lambda_{em}$ 442 nm (PBS)

V07-09144 differs from V07-09111 by having a change in position of one of the sulfo groups. Their respective fluorescence intensities are comparable, however, V07-09144 shows a 50% lower binding in a functional plate assay.

Synthesis and properties of representative compounds were as follows.

EXAMPLE 1

Synthesis of 3-(7-ethoxycarbonylamino-4-oxo-1,2,3,4-tetrahydro-cyclopenta[c]chromen-1-yl)propionic acid ethylester (V07-09096)

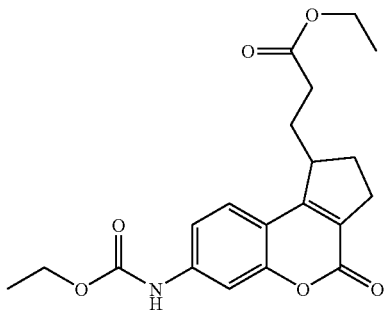

W=—O—CH$_2$—CH$_3$
n=1
R$^1$, R$^2$, R$^3$, R$^4$=H
X=—CH$_2$—CH$_2$—
R5=—C(O)—O—CH$_2$—CH$_3$

Two g 3-ethoxycarbonylamino-phenol and 3.0 g 3-ethoxycarbonylethyl-2-oxo-cyclopentane-carboxylic acid ethylester were dissolved in 42 g of 75% sulfuric acid. After stirring at 22° C. for 72 hours the mixture was poured into 200 ml water. The resulting oil was separated from the aqueous solution and treated several times with water. After removal of the water, the residue was dissolved in ethanol, filtered, and the solvent was removed.

Yield: 1.8 g of a dark oil
$\lambda_{max}$ 328 nm; $\lambda_{em}$ 393 nm
$\epsilon$=23.00 (in methanol).
MS ES$^+$: 374 (base, M+H$^+$)

EXAMPLE 2

Synthesis of 3-(7-amino-4-oxo-6-sulfo-1,2,3,4-tetrahydro-cyclopenta[c]chromen-1-yl)-3-sulfopropionic acid bis sodium salt (V07-09089)

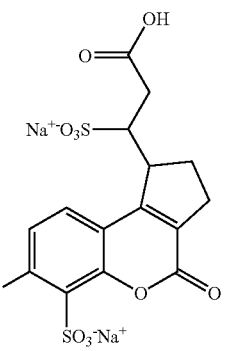

8-isomer
X=—CH$_2$—CH$_2$—
n=1
W=—OH
R$^1$ and R$^3$=—SO$_3$M, M=Na$^+$
R$^2$, R$^4$, and R$^5$=H To 1 g of 3-(7-ethoxycarbonylamino-4-oxo-1,2,3,4-tetrahydro-cyclopenta[c]chromen-1-yl)-propionic acid ethyl-ester was added 10 ml 30% oleum at 0° C. The mixture was heated at 70° C. for ten hours. After cooling, the dark oil was poured onto crushed ice.

The resulting solution was purified by reverse phase chromatography. The elution was carried out beginning with water containing 0.5% hydrochloric acid, to water acetonitrile mixture 70/30 containing 0.5% hydrochloric acid.

The blue fluorescent main product occurred as a pair of two diastereoisomers. The corresponding fractions were collected, neutralized with sodium hydrogencarbonate, and the solvent removed to a residue of 100 ml.

To remove salts, the solution was subjected to a neutral reverse phase chromatography column and eluted with water. The fluorescent product fractions were collected, the solvent was removed, and the residue was dried in vacuo.

Yield: 300 mg of a yellowish gray powder
UV-Vis (PBS): $\lambda_{max}$ 352 nm; $\lambda_{em}$ 429 nm
MS ES$^-$: 215.5 (base, M$^{2-}$); 432 (50%, M$^{2-}$+H$^+$); 454 (30%, M$^{2-}$+Na$^+$)

EXAMPLE 3

Synthesis of 3-(7-amino-4-oxo-8-sulfo-1,2,3,4-tetrahydro-cyclopenta[c]chromen-1-yl)-3-sulfo propionic acid bis sodium salt (V07-09142)

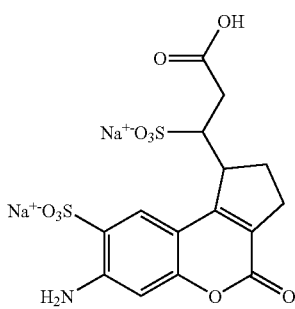

6-isomer
X=—CH$_2$—CH$_2$—
n=1
W=—OH
R$^1$ and R$^2$=—SO$_3$M, M=Na$^+$
R$^3$, R$^4$, and R$^5$=H To 1 g of 3-(7-ethoxycarbonylamino-4-oxo-1,2,3,4-tetrahydro-cyclopenta[c]chromen-1-yl)-propionic acid ethyl-ester was added 10 ml 30% oleum at 0° C. The mixture was heated at 100° C. for two hours. After cooling the dark oil was poured onto crushed ice.

The resulting solution was purified by reverse phase chromatography. The elution was carried out beginning with water containing 0.5% hydrochloric acid to water acetonitrile mixture 70/30 containing 0.5% hydrochloric acid.

The blue fluorescent main product occurred as a pair of two diastereoisomers. The corresponding fractions were collected, neutralized with sodium hydrogencarbonate and the solvent removed to a residue of 100 ml.

To remove salts, the solution was subjected to a neutral reverse phase chromatography column and eluted with water. The fluorescent product fractions were collected, the solvent was removed and the residue was dried in vacuo.

Yield: 220 mg of a yellowish gray powder
UV-Vis (PBS): $\lambda_{max}$ 349 nm, $\lambda_{em}$ 440 nm
MS ES$^-$: 215.5 (base, M$^{2-}$); 432 (50%, M$^{2-}$+H$^+$); 454 (30%, M$^{2-}$+Na$^+$)

EXAMPLE 4

Synthesis of 3-(7-amino-4-oxo-6,8-disulfo-1,2,3,4-tetrahydro-cyclopenta[c]chromen-1-yl)-3-sulfo-propionic acid tris sodium salt (V07-09140)

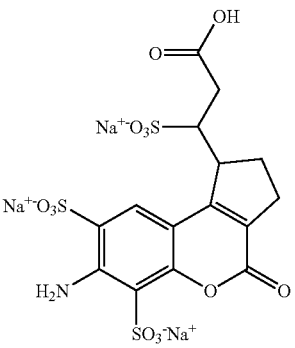

6, 8-isomer
X=—CH$_2$—CH$_2$—
n=1
W=—OH
R$^1$, R$^2$, and R$^3$=—SO3M, M=Na$^+$
R$^4$ and R$^5$=H To 1 g of 3-(7-ethoxycarbonylamino-4-oxo-1,2,3,4-tetrahydro-cyclopenta[c]chromen-1-yl)-propionic acid ethyl-ester was added 15 ml 30% oleum at 0° C. The mixture was heated at 100° C. for 4 hours. After cooling the dark oil was poured onto crushed ice.

The resulting solution was purified by reverse phase chromatography. The elution was carried out beginning with water containing 0.5% hydrochloric acid to water acetonitrile mixture 70/30 containing 0.5% hydrochloric acid.

The very polar blue fluorescent main product occurred as a pair of two diastereoisomers, which were not separated on the column. The corresponding fractions were collected, neutralized with sodium hydrogencarbonate and the solvent removed to a residue of 100 ml.

To remove salts, the solution was subjected to a neutral reverse phase chromatography column and eluted with water. The fluorescent product fractions were collected, the solvent was removed and the residue was dried in vacuo.

Yield: 80 mg of a brownish powder.
UV-Vis (PBS): $\lambda_{max}$ 350 nm, $\lambda_{em}$ 435 nm.
MS ES$^-$: 170.2 (base, M$^{3-}$); 255.5 (30%, M$^{3-}$+H$^+$); 266.6 (10%, M$^{3-}$+Na$^+$).

EXAMPLE 5

Synthesis of 3-(7-amino-4-oxo-6-sulfo-1,2,3,4-tetrahydro-cyclopenta[c]chromen-1-yl)-3-sulfo propionic acid NHs ester bis sodium salt (V07-09089-NHS)

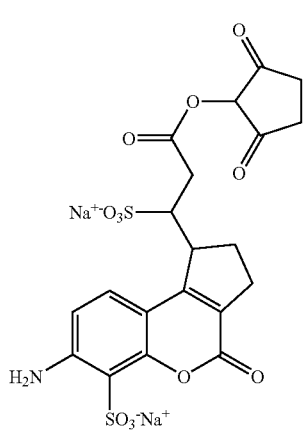

8-isomer
X=—CH$_2$—CH$_2$—
n=1
W=—O—NHS
R$^1$ and R$^3$=—SO$_3$M, M=Na$^+$
R$^2$, R$^4$, and R$^5$=H 140 mg of 3-(7-Amino-4-oxo-6-sulfo-1,2,3,4-tetrahydro-cyclopenta[c]chromen-1-yl)-3-sulfo-propionic acid bis sodium salt were dissolved in 6 ml dimethylformamide. After addition of 140 mg TSTU and 240 µl of DIPEA the solution was stirred for 1 hour. The solvent was removed in vacuo and the residue was purified by reverse phase column chromatography. Elution was carried out with water containing 0.5% trifluoracetic acid to water acetonitrile mixture 70/30 containing 0.5% trifluoracetic acid.

The corresponding fractions were collected and the solvent was removed. After dying in vacuum the oily residue was treated several times with diethylether. The stability of this NHS ester was low.

Yield: 110 mg of a yellowish powder

UV-Vis (PBS): $\lambda_{max}$ 350 nm, $\lambda_{em}$ 430 nm.

MS ES$^-$: 264 (base, M$^{2-}$).

EXAMPLE 6

Synthesis of 4-[3-(7-amino-4-oxo-6-sulfo-1,2,3,4-tetrahydro-cyclopenta[c]chromen-1-yl)-3-sulfo-propionylamino]-butyric acid (V07-09111)

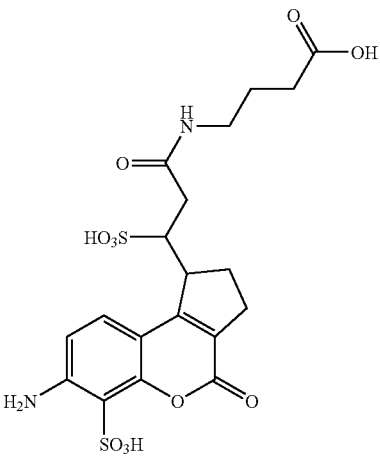

8-isomer
X=—CH$_2$—CH$_2$—
n=1
W=—NH—CH$_2$—CH$_2$—CH$_2$—COOH
R$^1$ and R$^3$=—SO$_3$M, M=H$^+$
R$^2$, R$^4$, and R$^5$=H 140 mg of 3-(7-amino-4-oxo-6-sulfo-1,2,3,4-tetrahydro-cyclopenta[c]chromen-1-yl)-3-sulfo-propionic acid bis sodium salt were dissolved in 6 ml dimethylformamide. After addition of 140 mg TSTU and 240 µl of DIPEA the solution was stirred for one hour.

This mixture was added to a solution of 145 mg 4-aminobutyric acid and 240 µl DIPEA in 6 ml water. After one additional hour the solvent was removed in vacuo and the residue was purified by reverse phase column chromatography. Elution was carried out with water containing 0.5% trifluoracetic acid to water acetonitrile mixture 70/30 containing 0.5% trifluoracetic acid.

The corresponding fractions were collected and the solvent was removed. After dying in vacuum the oily residue was treated several times with diethylether.

Yield: 110 mg of a yellowish powder.

UV-Vis (PBS): $\lambda_{max}$ 352 nm, $\lambda_{em}$ 430 nm.

MS ES$^-$: 258 (base, M$^{2-}$); 517.2 (M$^{2-}$+H$^+$); 539 (30%, M$^{2-}$+Na$^+$).

EXAMPLE 7

Synthesis of 4-[3-(7-amino-4-oxo-6-sulfo-1,2,3,4-tetrahydro-cyclopenta[c]chromen-1-yl)-3-sulfo-propionylamino]-butyric acid NHS ester bis diisopropylethylammonium salt (V07-09111-NHS)

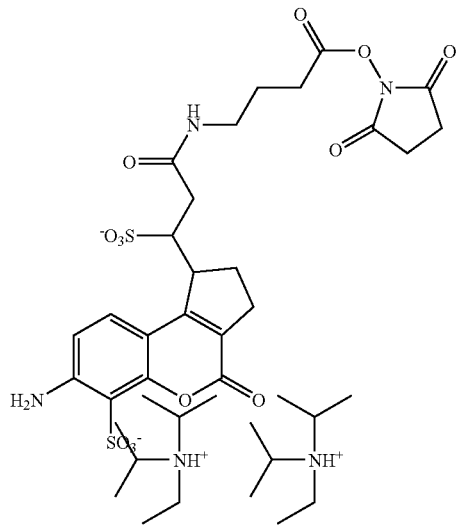

8-isomer
X=—CH$_2$—CH$_2$—
n=1
W=—NH—CH$_2$—CH$_2$—CH$_2$—COO—NHS
R$^1$ and R$^3$=—SO$_3$M, M=DIPEA-H$^+$
R$^2$, R$^4$, and R$^5$=H 30 mg of 4-[3-(7-amino-4-oxo-6-sulfo-1,2,3,4-tetrahydrocyclopenta[c]chromen-1-yl)-3-sulfo-propionylamino]-butyric acid were dissolved in 3 ml dimethylformamide. After addition of 23 mg TSTU and 20 µl of DIPEA the solution was stirred for 15 minutes. The solvent was removed in vacuo and the residue was purified by reverse phase column chromatography. Elution was carried out with water to 70/30 water acetonitrile mixture.

The corresponding fractions were collected and the solvent was removed. After dying in vacuum the oily residue was treated several times with diethylether.

Yield: 22 mg of a yellowish powder.
UV-Vis (PBS): $\lambda_{max}$ 352 nm, $\lambda_{em}$ 430 nm.
MS ES$^-$: 306.6 (base, M$^{2-}$); 614.2 (M$^{2-}$+H$^+$); MS ES$^+$: 130 (base, diisopropyethylammonium).

EXAMPLE 8

Figure 1:
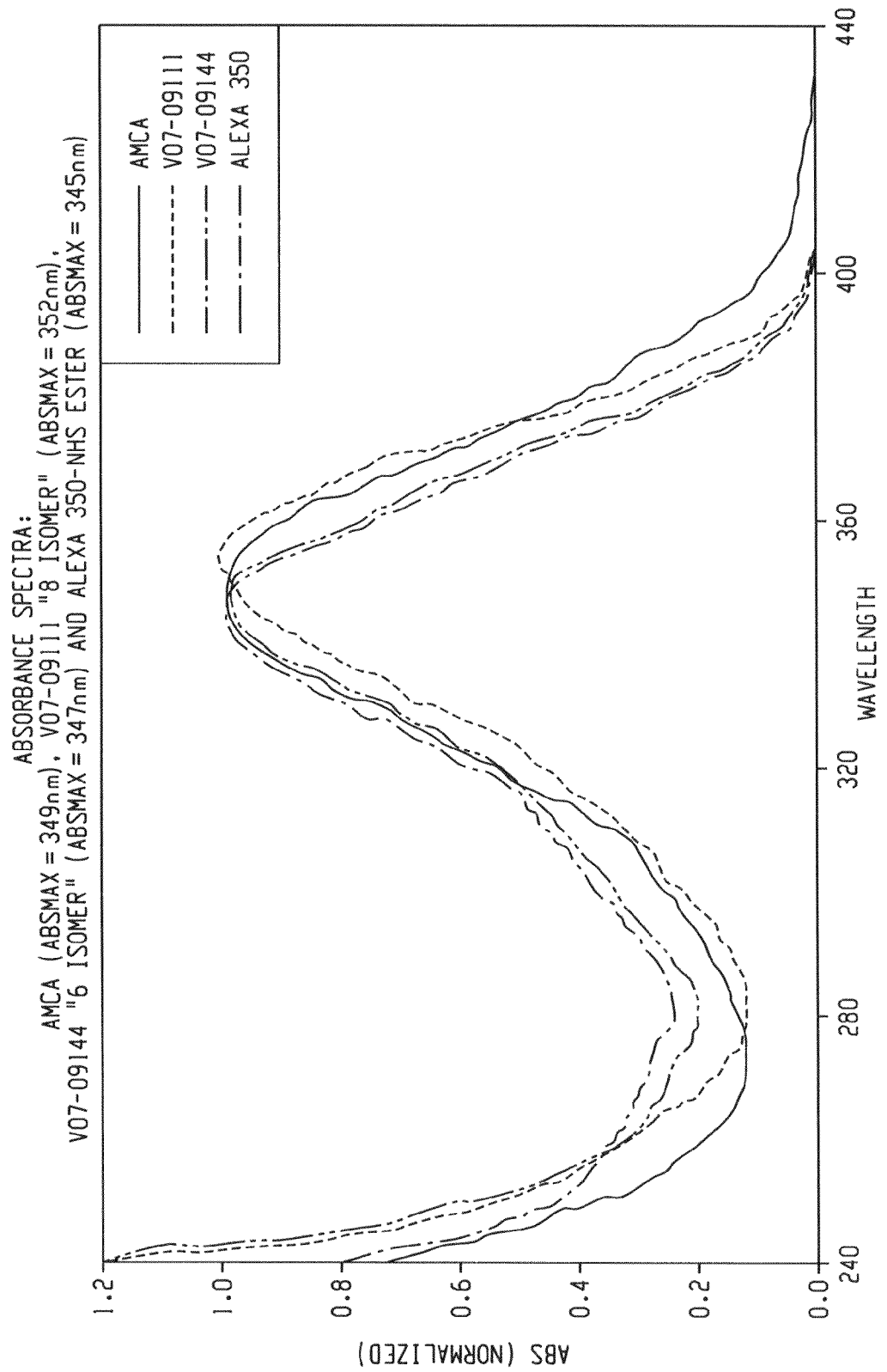
FIG. 1 shows absorbance specta of 7-amino-4-methyl-3-coumarinylacetic acid (AMCA), V07-09111 "8-isomer", V07-09144 "6-isomer" and Alexa Fluor 350-NHS ester.

Absorbance Spectra of V07-9111-NHS "8-isomer", V07-09144-NHS "6-isomer", succinimidyl-7-amino-4-methylcoumarin-3-acetate (NHS-AMCA) and Alexa Fluor 350-NHS Each of NHS-AMCA (MW=330 g/mole), V07-09111-NHS "8-isomer" (MW=874.1 g/mole), V07-0144-NHS "6-isomer" (MW=874.1 g/mole) and Alexa Fluor 350-NHS, Molecular Probes (Product #A10168) were reconstituted in DMF at 10 mg/ml and then diluted 1:1000 in PBS buffer (100 mM sodium phosphate, 150 mM NaCl; pH 7.2). Absorbance of the sample was evaluated from 440 nm to 240 nm on a UV Cary Spectrophotometer (Varian). Absorbance (Abs) spectra of the compounds dissolved in PBS buffer are shown in FIG. 1. The results showed absorbance maxima (Abs$_{Max}$)=352 nm for V07-09111-NHS "8-isomer", Abs$_{Max}$=347 nm for V07-0144-NHS "6-isomer", Abs$_{Max}$=349 nm for NHS-AMCA, and Abs$_{Max}$=345 nm for Alexa Fluor 350-NHS, all of which were within 7 nm of each other.

EXAMPLE 9

Absorption Spectra of Compounds V07-09111 "8-isomer" and V07-09144 "6-isomer"

Absorption spectra of compounds V07-09111 and V07-09144 (concentrations between 10 µM and 50 µM) in water and ethanol (spectral grade) were recorded (Analytik Jena Specord 205 absorption spectrometer, quartz cuvettes with a pathlength of 1 cm). For emission spectra determination, the solutions were diluted in PBS (100 mM, pH 7.4, 100 mM sodium chloride, 5 mM sodium azide) to an absorbance of around 0.1 at a 1 cm pathlength; emission spectra were recorded on a JASCO FP-6600 fluorescence spectrometer; excitation wavelength 345 nm, excitation and emission slits were 3 nm and 6 nm, respectively. Both absorption and emission spectra were normalized to the maxima for presentation in FIGS. 2, 3, 4, and 5.

Figure 2:
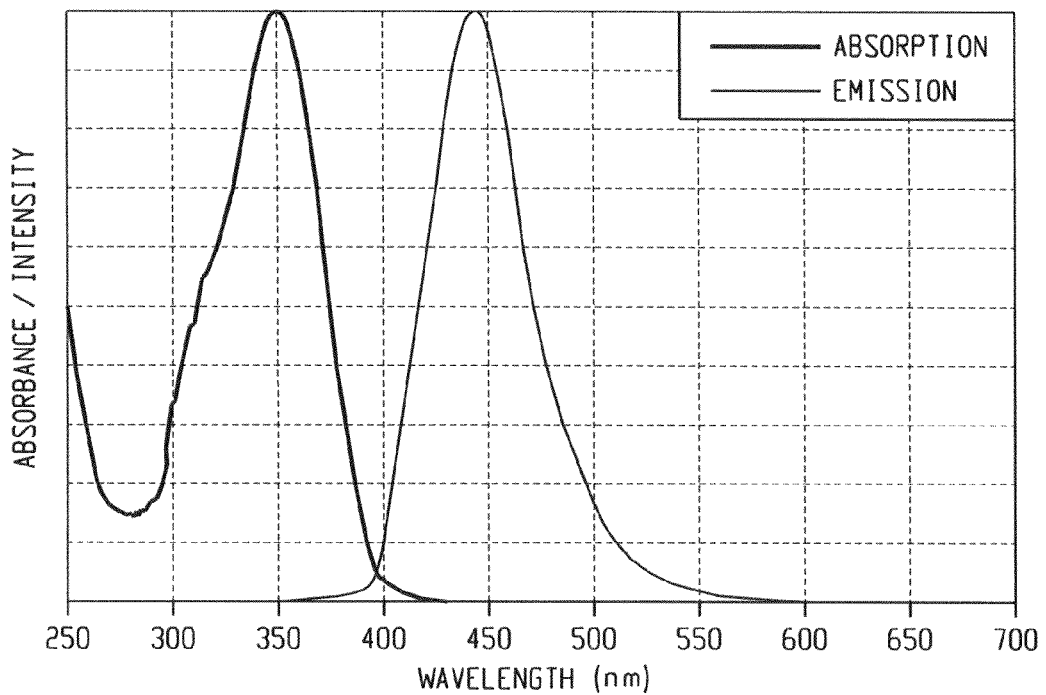
FIG. 2 shows absorption and emission spectra of compound V07-09144 in water.
Figure 3:
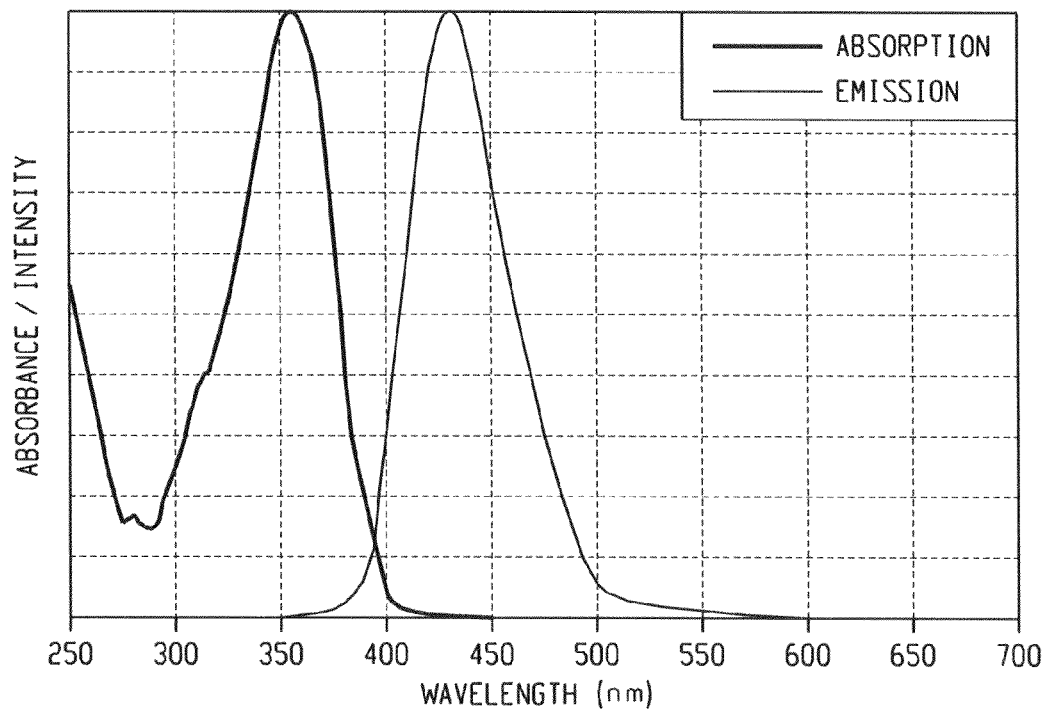
FIG. 3 shows absorption and emission spectra of compound V07-09144 in ethanol.
Figure 4:
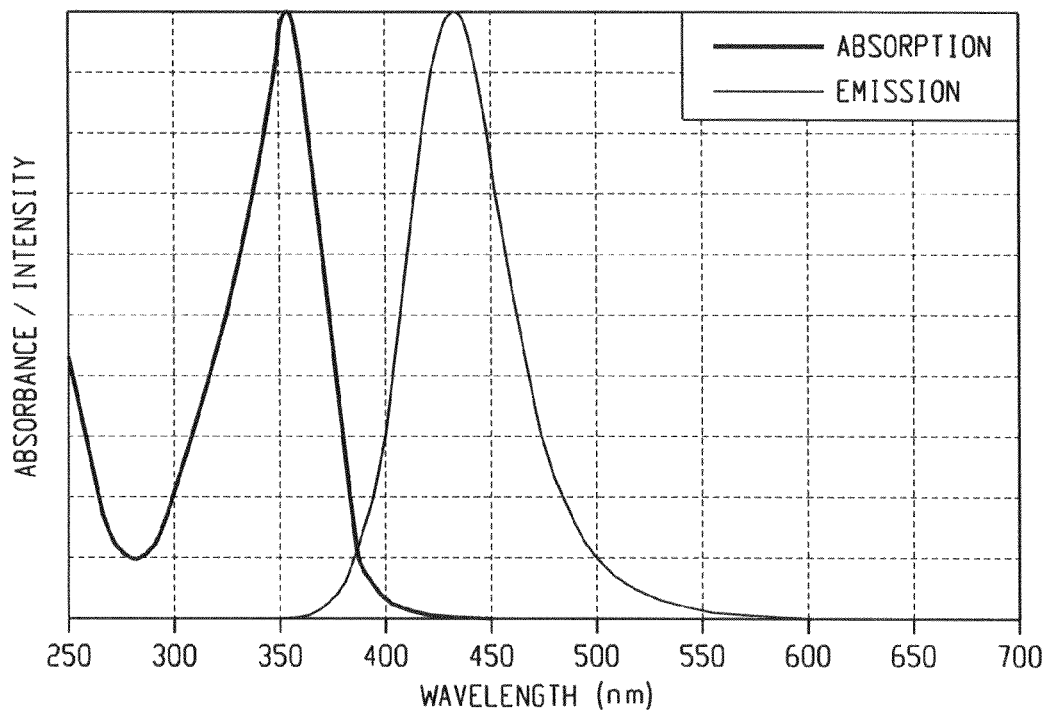
FIG. 4 shows absorption and emission spectra of compound V07-09111 in water.
Figure 5:
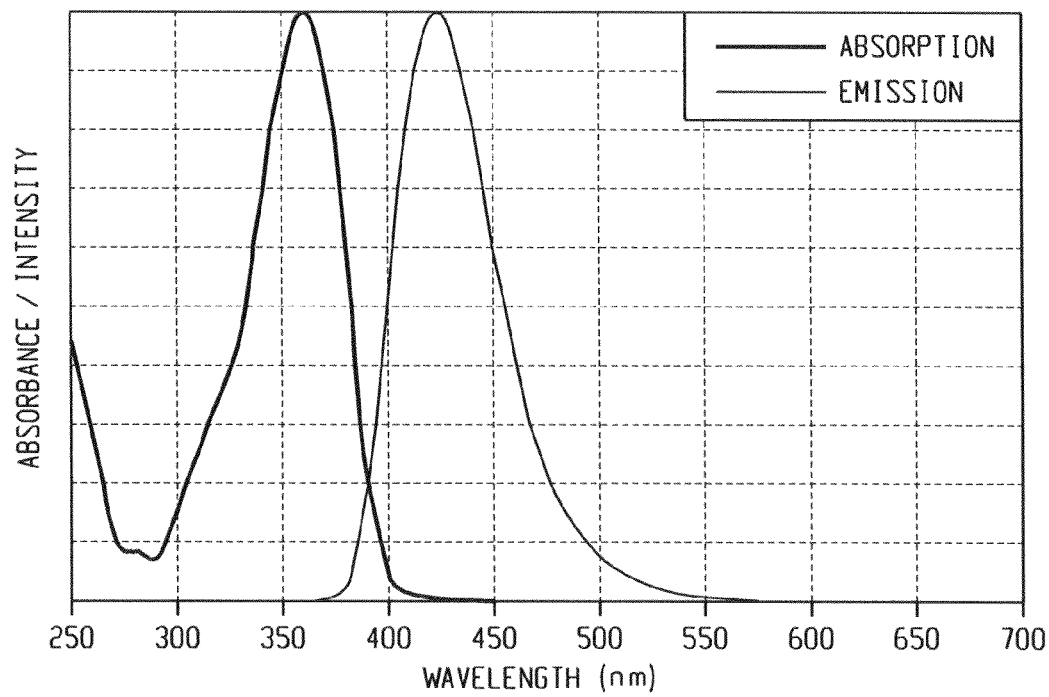
FIG. 5 shows absorption and emission spectra of compound V07-09111 in ethanol.

FIGS. 2 and 3 show the absorbance and emission spectra of V07-09144 in water and ethanol, respectively. FIGS. 4 and 5 show the absorbance and emission spectra of V07-09111 in water and ethanol, respectively. The absorbance and emission spectra of V07-09111 are 350 nm and 430 nm in water, and 351 nm and 443 nm in ethanol, respectively. The absorbance and emission spectra of V07-09144 are 350 nm and 440 nm in water, and 351 nm and 443 nm in ethanol, respectively.

EXAMPLE 10

Fluorescence Intensity Displayed by NHS-AMCA, V07-09111-NHS "8-isomer", V07-09144-NHS "6-isomer", and Alexa Fluor 350-NHS V07-09111-NHS "8-isomer", V07-09144-NHS "6-isomer", NHS-AMCA and Alexa Fluor 350-NHS were reconstituted in DMF at 10 mg/ml and diluted 1:250 in PBS buffer (100 mM sodium phosphate, 150 mM NaCl; pH 7.2) and analyzed on a UV Cary Spectrophotometer (Varian). Each sample was then adjusted with PBS buffer so that their values at Abs$_{Max}$ matched. Each of the dye samples was added to the wells of 96-well white opaque plates (100 µl/well; triplicates) and the fluorescence intensity was measured on Tecan Safire using optimal Alexa Fluor 350 setting (ex 346/em 442) and V07-09111-NHS "8-isomer"/V07-09144-NHS "6-isomer" setting (ex 353 nm/em 432 nm). The fluorescence intensity was normalized to NHS-AMCA. The data are presented in FIGS. 6A and B. The results showed higher fluorescence intensity displayed by the V07-09111-NHS "8-isomer" and V07-09144-NHS "6-isomer" compared to Alexa Fluor 350-NHS and NHS-AMCA at excitation of 353 nm and emission 432 nm settings (FIG. 6B). At 346 nm and 442 nm settings (FIG. 6A), V07-09111 was similar in fluorescence intensity to Alexa Fluor 350 and V07-09144 was superior to Alexa Fluor 350.

EXAMPLE 11

Protein Labeling of V07-9111-NHS "8-isomer", V07-0144-NHS "6-isomer", NHS-AMCA, and Alexa Fluor 350-NHS One mg of goat anti-mouse heavy and light (H+L) IgG (GAM) in PBS buffer pH 7.6 at 10 mg/ml, and 1 mg of streptavidin (SA) at 10 mg/ml in 50 mM borate buffer pH 8.5 were labeled with each dye using the following molar excesses:

|  | GAM (PBS pH 7.6) | SA (50 mM Borate Buffer pH 8.5) |
|---|---|---|
| NHS-AMCA | 7.5X, 10X, 12.5X, 15X | 7.5X, 10X |
| V07-09111-NHS "8-isomer" | 7.5X, 10X, 12.5X, 15X | 7.5X, 10X |
| V07-09144-NHS "6-isomer" | 7.5X, 10X, 12.5X, 15X | 7.5X, 10X |
| Alexa Fluor 350-NHS | 7.5X, 10X, 12.5X, 15X | 7.5X |

The reaction was carried out for one hour protected from light. After one hour incubation, the conjugates were adjusted with PBS buffer to a total volume of about 500 µl. The unreacted dye was removed using Fluorescent Dye Removal Resin (Thermo Scientific). The conjugates were diluted 1:10 in PBS buffer and analyzed on a UV Cary Spectrophotometer (Varian) from 230-425 nm. Based upon $OD_{280}$ and absorbance maxima for each conjugate, the concentrations and mole dye to mole protein ratios were determined.

|  | 7.5X | 10X | 12.5X | 15X |
|---|---|---|---|---|
| GAM-AMCA | 2.1 | 2.9 | 2.6 | 3.0 |
| GAM-V07-09111 | 7.1 | 9.2 | 11.1 | 12.3 |
| GAM-V07-09144 | 6.4 | 7.9 | 8.7 | 10.2 |
| GAM-Alexa Fluor 350 | 5.9 | 6.9 | 8.2 | 9.1 |

|  | 7.5X | 10X |
|---|---|---|
| SA-AMCA | 2.3 | 3.3 |
| SA-V07-09111 | 5.1 | 6.1 |
| SA-V07-09144 | 3.9 | 4.8 |
| SA-Alexa Fluor 350 | 4.0 | N/A |
| Alexa Fluor 350-GAM (Molecular Probes) | 5.8 |  |
| Alexa Fluor 350-SA (Molecular Probes) | 5.0 |  |

As shown in the tables above, the highest incorporation of dye was obtained with V07-09111-NHS, followed by Alexa Fluor 350-NHS and V07-09144-NHS.

EXAMPLE 12

Figure 7B:
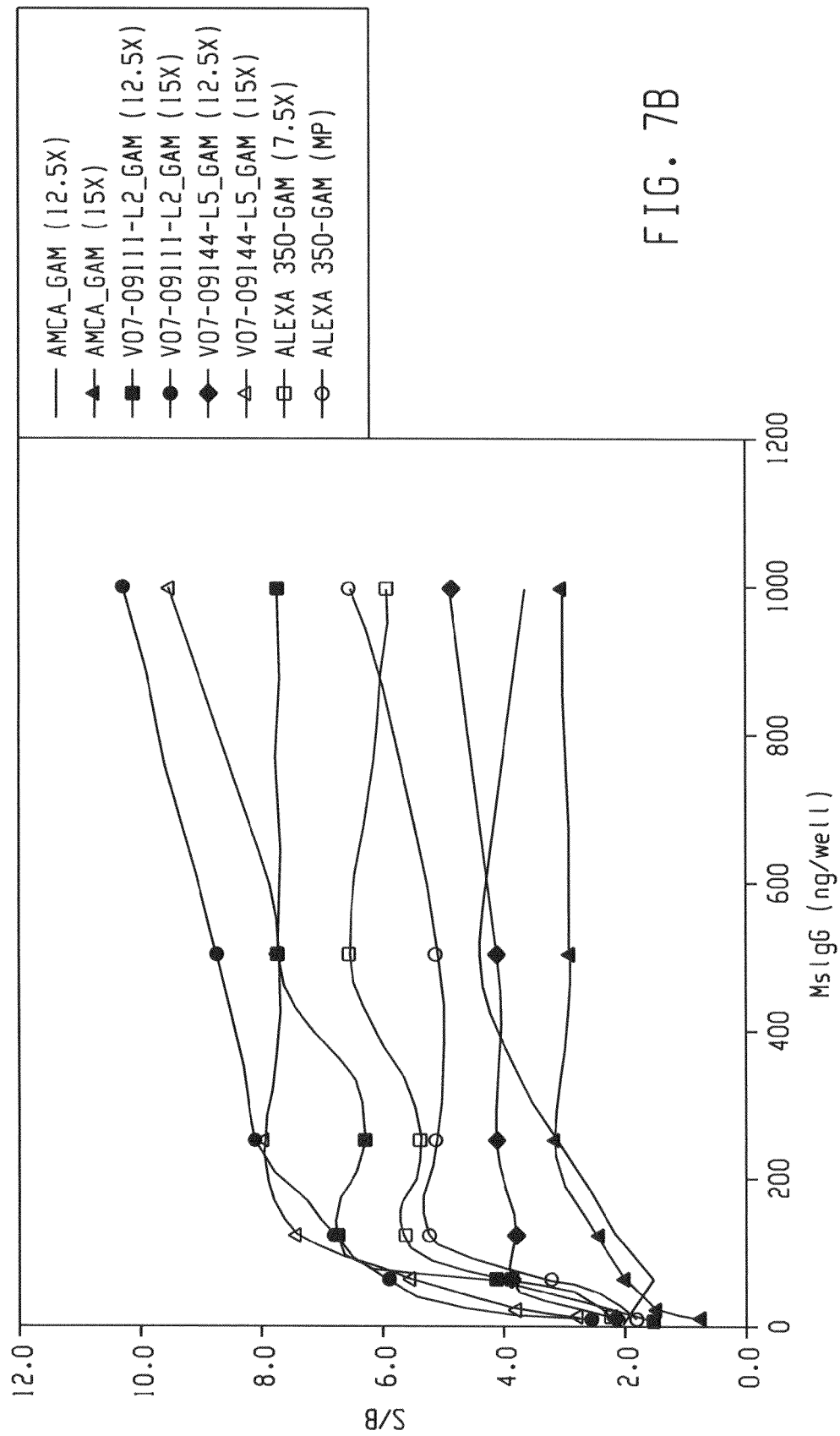
Figure 7C:
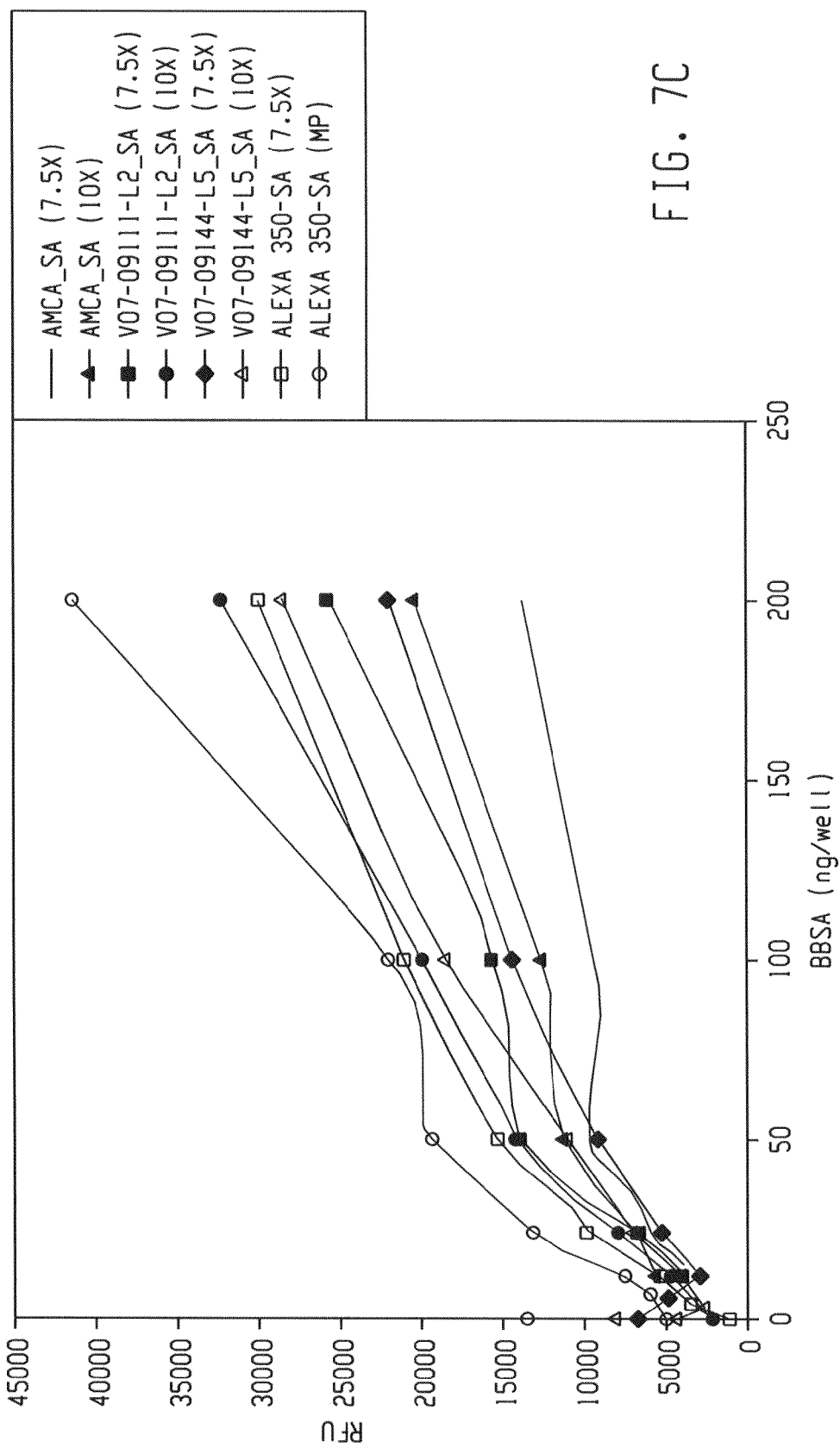
Figure 8:
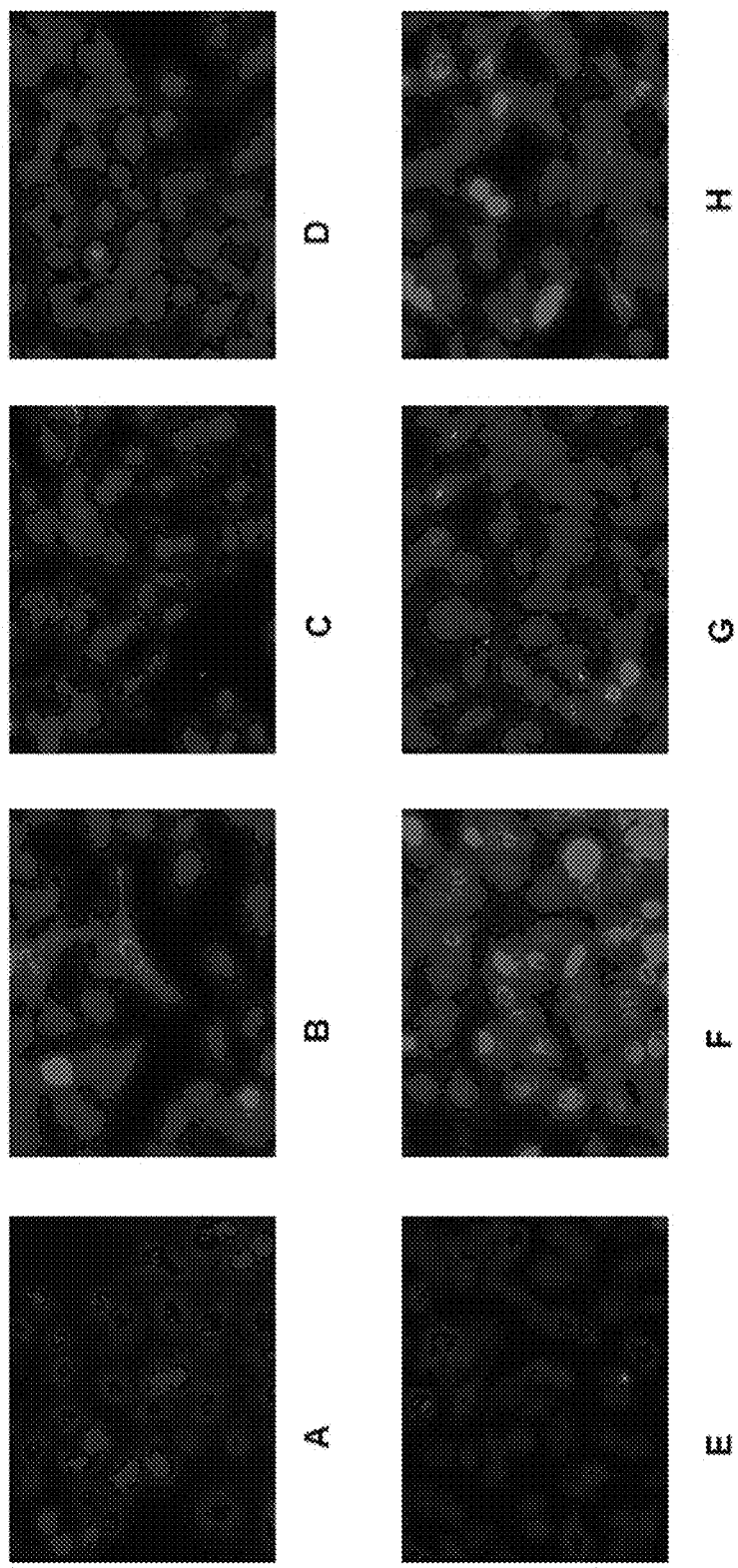

Plate-Based Functional Testing of Conjugates made with V07-09111-NHS "8-isomer", V07-09144-NHS "6-isomer", NHS-AMCA, and Alexa Fluor 350-NHS Streptavidin and GAM conjugates made in Example 11 were analyzed on biotin and mouse IgG coated white 96-well plates. The plates were coated by making a 1:1 serial dilution of biotinylated bovine serum albumin (BSA, Thermo Scientific) and mouse IgG with starting concentrations of 2 µg/ml and 10 µg/ml, respectively. One hundred µl of each dilution was added per well. The last column on each plate was considered blank (PBS buffer only). The plates were incubated overnight at 4° C. and then blocked by washing 3×200 µl with SuperBlock Blocking Buffer in PBS (Thermo Scientific). Plates were washed 2×200 µl PBS-Surfact-Amp 20 and 1×100 µl PBS. All of the conjugates were diluted to 4 µg/ml in PBS buffer, added to the plates (100 µl/well) and incubated for one hour at room temperature ($R_T$) (about 20° C. to about 22° C.). The plates were then washed 2×200 µl with PBS containing 0.05% Surfact-Amp 20 and 1×200 µl PBS. Finally 100 µl PBS buffer was added to the wells. The fluorescence intensity of the bound conjugate was measured on Tecan Safire using optimal Alexa Fluor 350 setting (ex 346/em 442) and optimal gain. The results are presented in FIGS. 7A-7D. FIGS. 7A and 7B show relative fluorescent units (RFU) and signal to background ratios (S/B), respectively, of goat anti-mouse antibodies (GAM) conjugated to amino-methyl-coumarin-acetate (AMCA), V07-09111-NHS, V07-09144-NHS, and Alexa Fluor 350-NHS. FIGS. 7C and 7D show RFU and S/B, respectively, of streptavidin (SA) conjugated to AMCA, V07-09111, V07-09144, and Alexa Fluor 350. The results showed higher signal sensitivities and intensities with conjugates made with V07-09111-NHS, V07-09144-NHS, and Alexa Fluor 350-NHS, compared to conjugates made with AMCA-NHS.

EXAMPLE 13

Detection of Lamin A using AMCA-NHS, V07-09111-NHS "8-isomer", V07-09144-NHS "6-isomer" and Alexa Fluor 350-NHS conjugated Goat anti Mouse (GAM) (H+L) IgG in Immunofluorescence Applications Lamin A was stained in HeLa cells to compare V07-09111-GAM and V07-09144GAM to AMCA-GAM and Alexa Fluor 350-GAM. HeLa cells were seeded at about 10,000 cells/well in a 96-well clear bottom collagen coated tissue culture plate (BD Falcon BioCoat collagen) and cultured overnight. To fix the cells, the medium was removed and replaced at 100 µl/well with freshly prepared 4% paraformaldehyde (EMS Product #15710-S) diluted in 8 mM sodium phosphate, 2 mM potassium phosphate, 140 mM sodium chloride and 10 mM potassium chloride (PBS pH 7.4) and the cells were incubated at room temperature for 15 minutes. After 15 minutes, the cells were washed 3 times with PBS. After removal of PBS the cells were permeabilized with 100 µl/well of PBS containing 0.1% Surfact-Amps X-100. The permeabilization was carried out at room temperature (RT) for 15 minutes and then the cells were washed two times with PBS. The cells were blocked at RT for 30 minutes with (100 µl/well) PBS containing 0.1% Triton X-100 and supplemented with 2% of Blocker™ BSA (Thermo Scientific). The blocking solution was removed and replaced with 50 µl primary antibody diluted in blocking solution. The cells were incubated with mouse monoclonal anti-human lamin A diluted 1/100 (of 1 mg/ml) overnight at 4° C. or one hour at room temperature.

The cells were then washed three times with PBS and incubated in 50 µl of the corresponding fluor-labeled secondary antibody diluted in blocking solution at 4 µg/ml and incubated at RT for 45 minutes while being protected from light. After incubation time, the cells were washed three times with PBS.

The images shown in FIGS. 8A-H were acquired using the appropriate shift free optical filter set with a 2×0.4 objective on Zeiss Axio Observer Z1 fluorescence microscope using an ORCA-ER-1394 Hamamatsu, CCD Digital Camera and the AxioVison Release 4.7 Software. Filter sets: Hoechst/DAPI (excitation 350-365/emission 445±50 nm). FIG. 8 shows staining of Lamin A in Hela cells using AMCA-GAM (7.5x) FIG. 8A; V07-09111-GAM (7.5x) FIG. 8B; V07-09144-GAM (7.5x) FIG. 8C; Alexa Fluor 350-GAM (7.5x) FIG. 8D; AMCA-GAM (15x) FIG. 8E; V07-09111-GAM (15x) FIG. 8F; V07-09144-GAM (15x) FIG. 8G; and Alexa Fluor 350-GAM (conjugate obtained from Molecular Probes) FIG. 8H.

Conjugates made with the V07-09111-NHS "8-isomer" and V07-09144-NHS "6-isomer" showed higher specificity of staining for the target with lower background than those made with NHS-AMCA or NHS-Alexa Fluor 350 using similar molar excesses of the dyes for labeling in all cases.

EXAMPLE 14

Evaluation of V07-09111-NHS "8-isomer" in an Oligodeoxyribonucleotide (ODN) Duplex Fluorescence Resonance Energy Transfer (FRET) Assay The procedure was obtained from Zhang et al. PNAS 105 (2008) 4156-4161.

An oligonucleotide bearing 3'-hydroxyethyidithiopropyl linkers is conjugated with DyLight 680 maleimide by dissolving 30 nmol oligonucleotide in 100 μl 12 mM NaHCO$_3$. A 11 μl aliquot of 1 M DTT is added and the mixture is incubated for one hour at room temperature. A 20 μl aliquot of DyLight 680 maleimide (Thermo Scientific) at 5 mg/ml in DMSO is added in two increments within a period of one hour. After reacting in the dark overnight, the labeled oligonucleotide is purified by spin-chromatography using BioSpin P6 microcolumns, followed by reverse phase HPLC (see below), and finally, by ethanol/sodium acetate precipitation. The labeled oligonucleotide is dissolved in 160 μl 0.1 M sodium phosphate buffer, pH 7.5. For example, the following oligonucleotide sequences may be prepared:

(SEQ ID NO. 1)
3'-[DyLight 680-S]-GCC TTT CA G GGA GTA TCG A-5'

(SEQ ID NO. 2)
5'-CGG AAA GT [V07-09111-NHS] C CCT CAT AGC T-3'

A 10 nmol aliquot of amino linker-bearing corresponding oligonucleotide is dissolved in 30 μl of 0.1 M NaHCO$_3$. Two×7.5 μl portions of dye solutions (0.5 mg V07-09111-NHS "8-isomer" in 30 μl DMSO) are added over a one hour interval, and the homogeneous reaction mixture is left overnight at room temperature in the dark. The labeled oligonucleotide is purified by P6 spin-chromatography followed by reverse phase HPLC column (Microsorb MV100 C18, Varian, Lake Forest Calif.) eluted using a linear gradient of 2-50% acetonitrile in 0.1 M TEAA.

Oligodeoxyribonucleotide duplexes are prepared by mixing the oligonucleotides in a 1:1 molar ratio unless otherwise noted, in a buffer solution containing 25 mM Hepes, 1 mM MgCl$_2$, and 50 mM NaCl. The duplex mixtures are heated between 90-95° C. for five minutes to dissociate any intrastrand duplexes, and allowed to cool at room temperature to attain equilibrium.

FRET between V07-09111-NHS "8-isomer" and DyLight 680 will be observed when oligodeoxyribonucleotide duplexes are formed.

EXAMPLE 15

Figure 9:
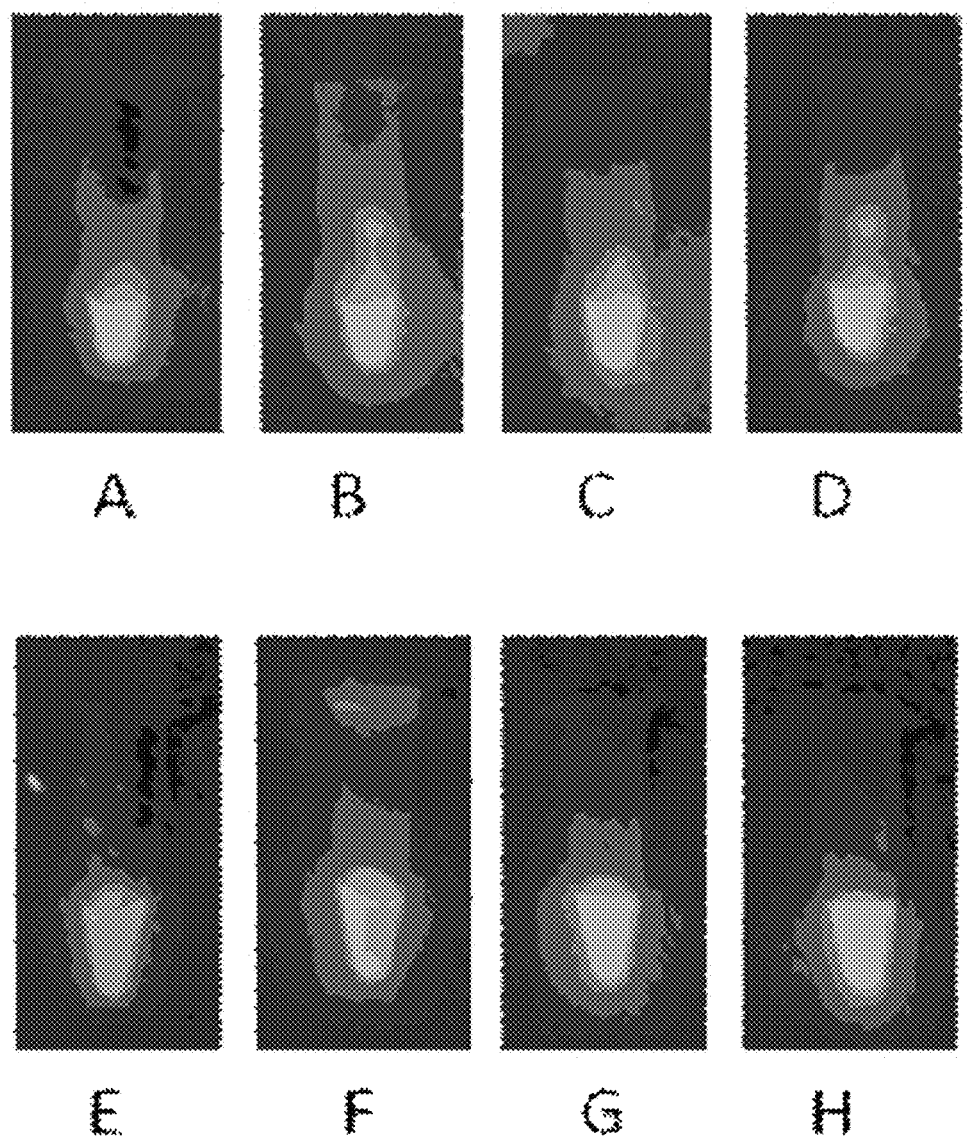

Demonstration of UV Excitation of AMCA-NHS, V07-09111-NHS "8-isomer", V07-09144-NHS "6-isomer" and Alexa Fluor 350-NHS Ester by Photographing Samples Irradiated with a Hand-Held UV Lamp To each vial containing 1 mg of goat anti mouse (H+L) IgG in PBS buffer pH 7.6 (tubes A-D), or 1 mg of streptavidin in 50 mM borate buffer pH 8.5 (tubes E-H) 7.5× molar excess of corresponding dye (reconstituted in DMF at 10 mg/ml) was added and mixed. The tubes containing the conjugates were placed in a dark room, irradiated with a hand-held UV lamp, and photographed. The images are shown in FIG. 9, in which tubes using AMCA-GAM (FIG. 9A); V07-09111-GAM (FIG. 9B); V0709144-GAM (FIG. 9C); Alexa Fluor 350-GAM (FIG. 9D); AMCA-SA (FIG. 9E); V07-09111-SA (FIG. 9F); V07-09144-SA (FIG. 9G); and Alexa Fluor 350-SA (FIG. 9H) are shown. The images captured by photography showed that the V07-09111, V07-09144, and Alexa-350 conjugates exhibited equivalent signal intensities when irradiated with UV light. All of these dyes exhibited higher signal intensities than the AMCA conjugates.

EXAMPLE 16

Plate-Based Functional Testing of GAM-V07-9111-SS—NHS Conjugates

V07-09111-SS—NHS is conjugated with GAM and optimized using the method described in Example 3. Conjugates are analyzed on mouse IgG-coated white 96-well plates. The plates are coated by making a 1:1 serial dilution of mouse IgG, starting concentrations of 10 μg/ml. A 100 μl aliquot of each dilution is added per well. The last column on each plate was is considered blank (PBS buffer only).

Plates are incubated overnight at 4° C. and then blocked by washing 3×200 μl with SuperBlock Blocking Buffer in PBS (Thermo Scientific). Plates are washed 2×200 μl PBS-Surfact-Amp 20 and 1×100 μl PBS. The conjugates are diluted to 4 μg/ml in PBS buffer, added to four rows of the plates (100 μl/well) and incubated for one hour at room temperature (RT). The plates are then washed 2×200 μl with PBS containing 0.05% Surfact-Amp 20 and 1×200 μl PBS. DTT (50 mM) is added to wells in duplicate rows, and 100 μl PBS buffer is added wells in the remaining duplicate rows. The plates are covered and incubated at 37° C. for 30 minutes. Fluorescence intensity of the bound conjugate is measured on Tecan Safire (excitation 346 nm, emission 442 nm) and optimal gain.

Wells that are incubated with DTT show a 5-15 fold increase in signal intensity and sensitivity, compared to wells that are not incubated with DTT. The release of the fluorescent dye from the antibody bound to the plate increases the fluorescent intensity due to decreased quenching.

EXAMPLE 17

V07-09111 "8-isomer" Coupled to Streptavidin (SA) as Donor and DY-481XL-biotin as Acceptor in a Fluorescence Resonance Energy Transfer (FRET) Assay A 1 μM solution of V07-0911-streptavidin conjugate with a mole dye to protein ratio (D/P)<6 in PBS was titrated with increasing amounts of DY-481XL-biotin (Dyomics GmbH, product number 481XL-30) up to an eightfold excess of the biotin conjugate.

Results are shown in FIG. 10. Due to the quenching effect of the streptavidin binding site and the low fluorescence intensity of the DY-481XL-biotin, only a decrease of the DY-350 emission was observed, but this decrease points to an efficient energy transfer between the donor dye DY-350 and the acceptor dye DY-481XL.

Applicants incorporate by reference the material contained in the accompanying computer readable Sequence Listing identified as SEQ_ST25.txt, having a file creation date of Jun. 15, 2009 9:20:19 A.M. and file size of 984 bytes.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. A compound of the formula

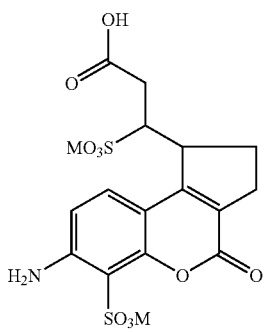

wherein M is selected from the group consisting of H⁺ and a biologically compatible cation.

2. A compound of the formula

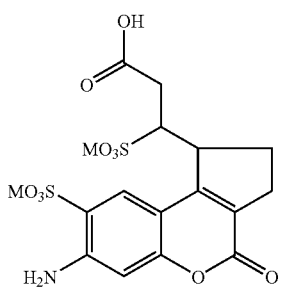

wherein M is selected from the group consisting of H⁺ and a biologically compatible cation.

3. A compound of the formula

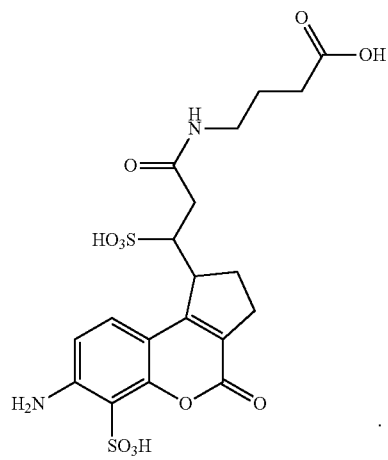

4. A compound of the formula

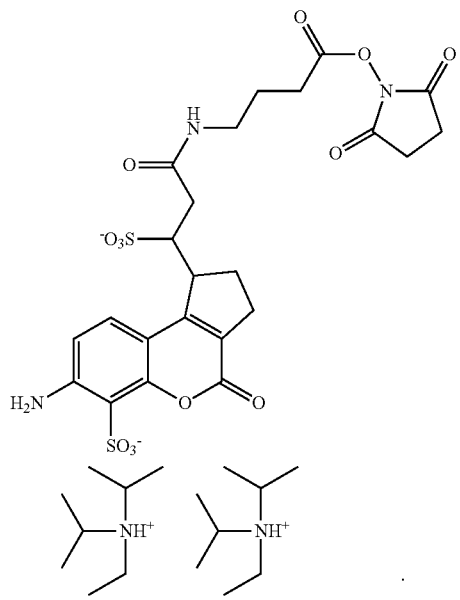

5. A compound of the formula

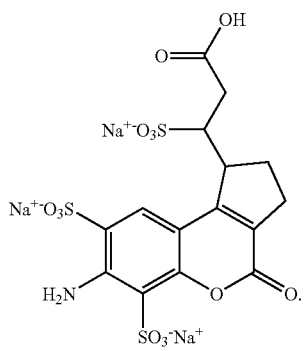

6. A compound of the formula

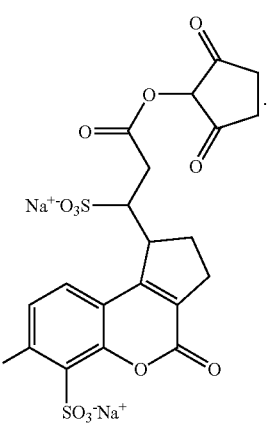

7. A method of using a compound for at least one of a bioanalytical or a diagnostic application, the method comprising contacting a biological sample with at least one of the compounds of claim 1, 2, 3, 4, 5, or 6, and qualitatively detecting the compound, quantitatively detecting the compound, or both qualitatively and quantitatively detecting the compound to result in the bioanalytical application.

8. The method of claim 7 wherein the application is selected from the group consisting of fluorescence resonance energy transfer, flow cytometry, tissue detection, and combinations thereof.

9. The method of claim 7 wherein tissue detection is by hand-held ultraviolet light detection.

* * * * *

UNITED STATES PATENT AND TRADEMARK OFFICE
CERTIFICATE OF CORRECTION

PATENT NO. : 8,039,648 B2  Page 1 of 1
APPLICATION NO. : 12/485439
DATED : October 18, 2011
INVENTOR(S) : Peter T. Czerney et al.

It is certified that error appears in the above-identified patent and that said Letters Patent is hereby corrected as shown below:

Title Page, item (54) and Col. 1, lines 1 and 2:

Currently the title on the face of the patent reads as:

"COMPOUNDS USED AS DYES COMPERABLE TO ALEXA FLUOR 350 DYES"

It should read:

"COMPOUNDS USED AS DYES COMPARABLE TO ALEXA FLUOR 350 DYES"

Signed and Sealed this
Sixth Day of December, 2011

David J. Kappos
*Director of the United States Patent and Trademark Office*